US007011648B2

(12) United States Patent
Breskot et al.

(10) Patent No.: US 7,011,648 B2
(45) Date of Patent: Mar. 14, 2006

(54) DEVICE FOR IMPLANTING CATHETERS

(75) Inventors: Tobias Breskot, Berlin (DE); Max Schaldach, deceased, late of Erlangen (DE); by Max Schaldach, Jr., legal representative, Berlin (DE)

(73) Assignee: Biotronik Mess-und Therapiegeraete GmbH & Co., Berlin (DE)

( * ) Notice: Subject to any disclaimer, the term of this patent is extended or adjusted under 35 U.S.C. 154(b) by 461 days.

(21) Appl. No.: 10/293,200

(22) Filed: Nov. 13, 2002

(65) Prior Publication Data
US 2003/0153925 A1 Aug. 14, 2003

(30) Foreign Application Priority Data
Nov. 20, 2001 (DE) ................. 101 58 289

(51) Int. Cl.
*A61M 5/178* (2006.01)
(52) U.S. Cl. .................. 604/164.05; 604/161
(58) Field of Classification Search ........... 604/170, 604/160–162, 164, 166, 166.01, 164.01–164.09
See application file for complete search history.

(56) References Cited

U.S. PATENT DOCUMENTS

| 4,345,606 A | 8/1982 | Littleford |
| 4,377,165 A | 3/1983 | Luther |
| 4,596,559 A | 6/1986 | Fleischhacker |
| 4,687,469 A | 8/1987 | Osypka |
| 4,955,859 A | 9/1990 | Zilber |
| 5,320,602 A * | 6/1994 | Karpiel ............... 604/514 |
| 5,681,274 A | 10/1997 | Parkins |
| 5,752,937 A | 5/1998 | Otten |
| 5,755,769 A | 5/1998 | Richard |
| 6,749,600 B1 * | 6/2004 | Levy ............... 604/527 |

FOREIGN PATENT DOCUMENTS

| DE | 23 43 094 | 3/1975 |
| DE | GM 79 28 830 U1 | 10/1979 |
| DE | 34 20 455 C1 | 5/1985 |
| DE | 199 36 207 A1 | 2/2001 |
| EP | 0 732 087 A1 | 3/1996 |
| FR | 2 688 288 A1 | 9/1993 |
| GB | 1 482 208 | 8/1977 |
| WO | WO 98/20812 A1 | 5/1998 |
| WO | WO 01/08599 A1 | 2/2001 |

* cited by examiner

*Primary Examiner*—Sharon Kennedy
(74) *Attorney, Agent, or Firm*—Hahn Loeser & Parks, LLP; John J. Cunniff

(57) ABSTRACT

A device for implanting catheters has a tube with a wall and a wire. The tube is intended to be introduced into a body so that at least one catheter can be inserted for implantation through the tube. The wall of the tube has an inside surface and an outside surface. The wire is preferably fixed at its first end in the region of the proximal end of the tube to the inside surface or the outside surface of the wall and the wire is guided in the proximity of that surface along the longitudinal direction of the tube from the proximal end of the tube to the distal end thereof and is then returned in the proximity of the respective other surface of the wall along the longitudinal direction from the distal end of the tube to the proximal end thereof. The wire is used to cut the tube open after insertion of the catheter.

18 Claims, 1 Drawing Sheet

DEVICE FOR IMPLANTING CATHETERS

The present invention concerns a device for implanting catheters having a tube with a wall which has inside surface and an outside surface and which encloses a cavity open both at the proximal end and at the distal end and which is adapted to be inserted into a body so that at least one catheter can be inserted for the implantation procedure through the tube. For that purpose the tube is of a length which is such that the proximal end of the tube remains outside a body of a patient upon insertion of a catheter.

BACKGROUND OF THE ART

Insertion cannulae are used to produce openings in the skin for the insertion of various medical devices into soft tissue or organs. For example an insertion cannula can be inserted through a needle puncture and a catheter can then be inserted by means of the cannula through the skin into the patient. After insertion of the catheter the cannula is removed from the patient again. In general terms in that respect the catheter is connected to a medical unit before the cannula is removed. In order to permit withdrawal of the cannulae in the proximal direction in spite of obstacles such as electrode plugs or catheter connections the cannula in the withdrawal operation is simultaneously torn open or cut open by means of a cutting tool which is disposed in proximal relationship.

U.S. Pat. No. 4,377,165 discloses a separable introduction device ("introducer"). That device has at a long side a desired-rupture location along which the introduction device can be severed for the removal thereof. In that case the desired-rupture location can be for example in the form of a notch, a perforation, holes or the like.

In that respect however it has been found that there is the disadvantage that the stability of the introduction device is reduced in order to provide the possibility of cutting open the introduction device. For example by virtue of its reduced stability the introduction device can be severed easily and at the wrong moment in time. Undesired severing of the introduction device can occur for example if the device is firstly introduced into the patient before the catheter has been completely inserted into the patient through the introduction device, before the catheter has been connected to the desired medical unit or before the introduction device has been removed from the patient and from the catheter.

In addition the above-described severable introduction device does not afford reliable severing and has a tendency to suffer from sharp edges when it is severed.

U.S. Pat. No. 5,752,937 discloses a medical introduction device. In that case the introduction device has a tube with a reinforcing strip or a wire which are let into the material of the tube and which extend substantially along the longitudinal axis of the tube. In that arrangement the reinforcing strip or the wire can be made from any suitable material which can be used as a cutting means which can be pulled along the longitudinal axis of the tube in order to cut open the introduction device and thereby to sever the introduction device for removal from the catheter. The reinforcing strip or the wire in that case presents a greater shearing force than the material of the tube of the introduction device. The operation of cutting open the introduction device by the reinforcing strip or the wire is effected by virtue of the difference in the levels of shearing strength.

That arrangement however has been found to suffer from the disadvantage that the entire longitudinal wall of the tube of the introduction device has to be cut through simultaneously.

Therefore the problem of the invention is to provide a device for implanting catheters, which can be easily cut open upon removal from the body without in that respect neglecting the necessary stability requirements.

SUMMARY OF THE INVENTION

That object is attained by a device for implanting catheters of the kind set forth in the opening part of this specification, having the characterizing features of accompanying claims.

In that respect the invention is based on the notion of providing a device for implanting catheters, which has a tube with a wall and a wire. In that case the tube is intended to be introduced into a body so that at least one catheter can be inserted for implantation through the tube. The wall of the tube has an inside surface and an outside surface. The wire is preferably fixed at its first end in the region of the proximal end of the tube to the inside surface or the outside surface of the wall and/or is let into the wall, the wire is then guided in the proximity of that surface along the longitudinal direction of the tube from the proximal end of the tube to the distal end thereof and is then returned in the proximity of the respective other surface of the wall along the longitudinal direction from the distal end of the tube to the proximal end thereof.

The advantages which the present invention entails are in particular that the implantation device is cut open by pulling the wire from the distal end towards the proximal end and thus is firstly cut open over the entire length. In that way friction between the implantation device and the implanted catheter is reduced and the operation of withdrawing of the implantation device after implantation of the catheter has been effected does not result in the implantation location and/or the implantation position of the catheter being endangered.

The fact that the tube is gradually cut open along its length means that the wire and the wall of the tube are exposed to substantially lower levels of stress, thereby preventing elastic deformation which in turn can endanger the implantation position of the implanted catheter.

Stability of the implantation device is further ensured by virtue of the fact that the tube can be made in one piece.

In an embodiment of the invention the second end of the wire is freely accessible at the proximal end of the tube. That provides that operation is simplified when cutting open the device.

In a preferred embodiment of the invention the device has two arms or plates at the proximal end of the tube. The arms serve to simplify handleability of the device, in particular when cutting it open. The provision of the two arms means that the operator can better hold the device firmly by means of the two arms when cutting it open.

In a further preferred embodiment of the invention the wire has a handle at its second end. By pulling on the handle the implantation device can be cut open from the distal end to the proximal end, which also facilitates handling of the device.

In a further embodiment of the invention the outside surface of the wall of the tube has a longitudinal slot which is adapted to guide the wire. The fact that the wire is guided in the longitudinal slot along the outside surface of the wall and that the wire is guided back at the inside of the wall ensures that the wire does not leave the implantation device and cannot cut into the surrounding vessel walls.

The length of the tube is dependent on the purpose thereof, namely serving as an insertion catheter. Suitable lengths are in the range of between 400 and 500 millimeters.

BRIEF DESCRIPTION OF THE DRAWINGS

An embodiment is described in greater detail hereinafter with reference to the FIGURE.

DETAILED DESCRIPTION OF A PREFERRED EMBODIMENT

Figure 1:
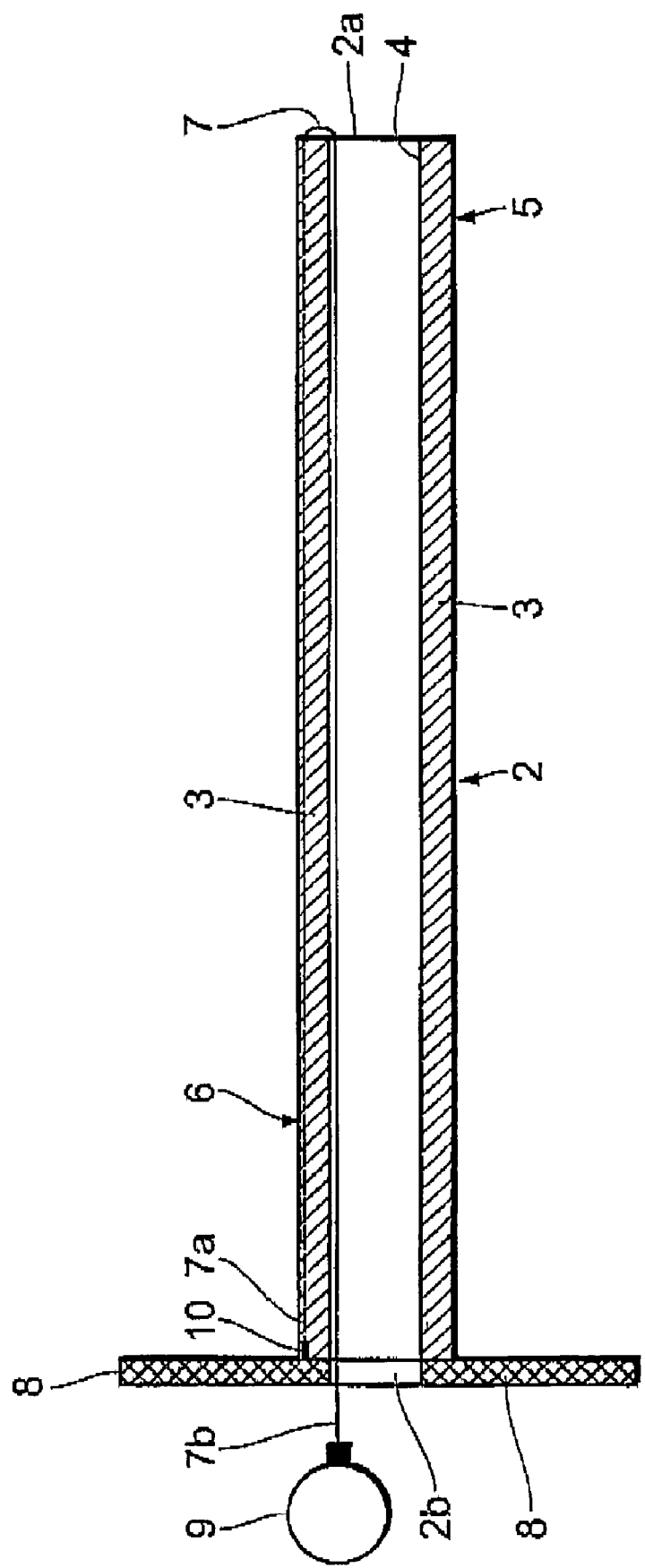
FIG. 1 shows a view in section of an implantation device.

FIG. 1 shows a tube 2 with a wall 3 and two arms 8 arranged at the proximal end 2b thereof. In addition at an outside surface 5 of the wall 3 the tube 2 has a longitudinal slot 6 along its longitudinal direction. The first end 7a of a wire 7 is fixed at a location 10 at the proximal end 2b of the tube 2. The wire 7 is then guided in the longitudinal slot 6 from the proximal end 2b of the tube 2 to the distal end 2a thereof. The wire 7 is then passed at the distal end 2a of the tube 2 around the distal end 2a and guided back at the inside surface 4 of the wall 3 from the distal end 2a of the tube 2 to the proximal end 2b thereof.

In that arrangement the length of the wire 7 is so selected that the second end 7b of the wire 7 projects out of the proximal end 2b of the tube 2. A handle 9 is preferably fixed to that second end 7b of the wire 7.

By applying a pulling force to the cable the wire 7 is pulled in the proximal direction and in that situation cuts through the wall 3 of the tube 2 along the length thereof. Preferably the wall 3 of the tube 2 of the implantation device is cut open along the length thereof prior to withdrawal of the implantation device. In that way the friction between the implantation device and a catheter to be implanted is reduced so that withdrawal of the implantation device does not adversely affect the implantation position of the catheter. The fact that the tube 2 is progressively cut open along its length means that the wire 7 and the wall 3 of the tube 2 are exposed to substantially lower levels of stress, thereby avoiding elastic deformation which in turn could endanger the implantation position of the implanted catheter.

The fact that the wire 7 is guided in the longitudinal slot 6 along the outside surface 5 of the wall 3 and that the wire 7 is guided back at the inside surface 4 of the wall ensures that the wire 7 does not leave the implantation device and does not cut into the surrounding vessel walls.

The invention claimed is:

1. A device for implanting a catheter in a body of a patient, the device comprising:
    a tube with an open proximal end, an open distal end and a wall, which has an inside surface and an outside surface and which encloses a cavity that is open both at the proximal end and at the distal end, and a longitudinal slot, adapted to guide the wire, in the outside surface of the wall,
    wherein the tube is adapted to be inserted into the body so that the catheter can be introduced for the implantation procedure through the tube,
    wherein the tube has a length such that the proximal end of the tube remains outside the patient's body upon insertion of a catheter, and
    wherein a wire extends in the proximity of one of the surfaces of the wall along a longitudinal direction of the tube from the proximal end to the distal end thereof and is guided back in the proximity of the respective other surface along the longitudinal direction from the distal end to the proximal end.

2. The device as set forth in claim 1, wherein:
    the length of the tube is between 400 and 500 mm.

3. The device as set forth in claim 1, wherein:
    the wire is at least partially embedded in the wall over its length from at least one of: the proximal end of the tube to the distal end thereof or the distal end of the tube to the proximal end thereof.

4. The device as set forth in claim 1, wherein:
    a first end of the wire is fixed in at least a region of the proximal end of the tube to at least one of the inside and outside surfaces of the wall.

5. The device as set forth in claim 1, wherein:
    a second end of the wire is freely accessible at the proximal end of the tube.

6. The device as set forth in claim 1, comprising:
    two arms at the proximal end of the tube.

7. The device as set forth in claim 5, comprising:
    a handle at the second end of the wire.

8. A device for implanting a catheter in a body of a patient, the device comprising:
    a tube with an open proximal end, an open distal end and a wall, the wall having an inside surface and an outside surface and enclosing a cavity through which the catheter may be introduced, the cavity being open both at the proximal end and at the distal end, a longitudinal slot positioned along the outside surface, the tube having a length in the range of from about 400 to 500 mm, two arms being located at the proximal end of the tube which remains outside the patient's body during insertion of the catheter; and
    a wire, having first and second ends, extending in the proximity of one of the surfaces of the wall along a longitudinal direction of the tube from the proximal end to the distal end thereof and guided back in the proximity of the respective other surface along the longitudinal direction from the distal end to the proximal end,
    the wire positioned in the longitudinal slot as the wire traverses the outside surface, the wire being embedded at least partially in the wall over its length from at least one of: the proximal end of the tube to the distal end thereof or the distal end of the tube to the proximal end thereof, the first end of the wire being fixed in at least a region of the proximal end of the tube to at least one of the inside and outside surfaces of the wall, and the second end of the wire freely accessible at the proximal end of the tube.

9. The device as set forth in claim 8, comprising:
    a handle at the second end of the wire.

10. An insertion cannula for introducing a catheter in a body of a patient, the cannula comprising:
    a tube with an open proximal end, an open distal end and a wall, which has an inside surface and an outside surface and which encloses a cavity that is open both at the proximal end and at the distal end,
    wherein the tube is adapted to be inserted into the body so that the catheter can be introduced for the implantation procedure through the tube,
    wherein the tube has a length such that the proximal end of the tube remains outside the patient's body upon insertion of a catheter, wherein a wire extends in the proximity of one of the surfaces of the wall along a longitudinal direction of the tube from the proximal end to the distal end thereof and is guided back in the proximity of the respective other surface along the longitudinal direction from the distal end to the proximal end, and wherein a first end of the wire is fixed in at least a region of the proximal end of the tube to at least one of the inside and outside surfaces of the wall.

11. The cannula as set forth in claim 10, wherein:
the length of the tube is between 400 and 500 mm.

12. The cannula as set forth in claim 10, wherein:
the wire is at least partially embedded in the wall over its length from at least one of: the proximal end of the tube to the distal end thereof or the distal end of the tube to the proximal end thereof.

13. The cannula as set forth in claim 10, wherein:
a second end of the wire is freely accessible at the proximal end of the tube.

14. The cannula as set forth in claim 10, additionally comprising:
two arms at the proximal end of the tube.

15. The cannula as set forth in claim 13, additionally comprising:
a handle at the second end of the wire.

16. The cannula as set forth in claim 10, additionally comprising:
a longitudinal slot, adapted to guide the wire, in the outside surface of the wall.

17. The cannula as set forth in claim 10, wherein:
the wire is at least partially embedded in the wall over its length from at least one of: the proximal end of the tube to the distal end thereof or the distal end of the tube to the proximal end thereof;

wherein a first end of the wire is fixed in at least a region of the proximal end of the tube to at least one of the inside and outside surfaces of the wall; and wherein a second end of the wire is freely accessible at the proximal end of the tube.

18. The cannula as set forth in claim 17, additionally comprising:
a longitudinal slot, adapted to guide the wire, in the outside surface of the wall.

* * * * *